(12) United States Patent
Wong (10) Patent No.: US 10,388,015 B2
(45) Date of Patent: Aug. 20, 2019

(54) AUTOMATED SEPTAL DEFECT DETECTION IN CARDIAC COMPUTED TOMOGRAPHY IMAGES

(71) Applicant: INTERNATIONAL BUSINESS MACHINES CORPORATION, Armonk, NY (US)

(72) Inventor: Chun Lok Wong, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 63 days.

(21) Appl. No.: 15/697,365

(22) Filed: Sep. 6, 2017

(65) Prior Publication Data

US 2019/0073764 A1    Mar. 7, 2019

(51) Int. Cl.
| | |
|---|---|
| G06K 9/00 | (2006.01) |
| G06T 7/00 | (2017.01) |
| G06T 7/136 | (2017.01) |
| G06T 7/162 | (2017.01) |
| G06T 7/174 | (2017.01) |
| G06T 7/62 | (2017.01) |
| G06N 20/00 | (2019.01) |

(52) U.S. Cl.
CPC .......... *G06T 7/0012* (2013.01); *G06N 20/00* (2019.01); *G06T 7/136* (2017.01); *G06T 7/162* (2017.01); *G06T 7/174* (2017.01); *G06T 7/62* (2017.01); *G01N 2800/325* (2013.01)

(58) Field of Classification Search
CPC ....... G06T 7/0012; G06T 7/174; G06T 7/162; G06T 7/136; G06T 7/62; G06N 20/00; G01N 2800/325
See application file for complete search history.

(56) References Cited

U.S. PATENT DOCUMENTS

| | | |
|---|---|---|
| 7,711,160 B2 | 5/2010 | O'Donnell et al. |
| 8,045,778 B2 | 10/2011 | Blaffert et al. |
| 8,150,119 B2 | 4/2012 | Zheng et al. |
| 8,700,126 B2 | 4/2014 | Li et al. |
| 2007/0276214 A1 | 11/2007 | Dachille et al. |
| 2009/0267941 A1 | 10/2009 | Von Berg et al. |
| 2017/0076449 A1 | 3/2017 | Chow et al. |

(Continued)

FOREIGN PATENT DOCUMENTS

WO    2004097720 A8    3/2005

OTHER PUBLICATIONS

Ananth V. Annapragada. "High-Resolution CT Vascular Imaging Using Blood Pool Contrast Agents," https://www.researchgate.net/publication/230666589_High-Resolution_CT_Vascular_Imaging_Using_Blood_Pool_Contrast_Agents.

(Continued)

*Primary Examiner* — Tom Y Lu
(74) *Attorney, Agent, or Firm* — Stephen J. Kenny; Erik Huestis; Foley Hoag LLP (57) ABSTRACT

Automated detection of septal defects in cardiac computed tomography images is provided. In various embodiments, a blood pool is extracted from a CTA image of a heart. The blood pool is determined to be a left pool. A septal curve of the left pool is extracted. A plurality of features of the septal curve is determined. The heart is classified as having an atrial septal defect, ventricular septal defect, or no defect based on the plurality of features.

20 Claims, 10 Drawing Sheets

(56) References Cited

U.S. PATENT DOCUMENTS

2017/0084029 A1* 3/2017 Piazza ................. A61B 5/1075
2017/0337343 A1* 11/2017 Kakadiaris ............. G06F 19/00

OTHER PUBLICATIONS

Li, S., Ross, I., Gill, S., Peters, T., Mahesh, P. and Rankin, R., Mar. 2007, Computer-aided septal defect diagnosis and detection. In Medical Imaging (pp. 65141A-65141A). International Society for Optics and Photonics.

* cited by examiner

AUTOMATED SEPTAL DEFECT DETECTION IN CARDIAC COMPUTED TOMOGRAPHY IMAGES

BACKGROUND

Embodiments of the present disclosure relate to automated septal defect detection, and more specifically, to computer-aided detection of septal defects in cardiac computed tomography images.

BRIEF SUMMARY

According to embodiments of the present disclosure, methods of and computer program products for septal defect detection are provided. In various embodiments, a blood pool is extracted from a computed tomography angiography (CTA) image of a heart. The blood pool is determined to be a left pool. A septal curve of the left pool is extracted. A plurality of features of the septal curve is determined. The heart is classified as having an atrial septal defect, ventricular septal defect, or no defect based on the plurality of features.

In various embodiments, a blood pool is extracted from a CTA image of a heart. The blood pool is determined to be a combined pool. A plurality of features of the combined pool is extracted. The heart is classified as having an atrial septal defect or ventricular septal defect based on the plurality of features.

DETAILED DESCRIPTION

Septal defects are congenital heart diseases developed during the formation of the heart. A septum is a wall of tissue, with the atrial septum separating the left and right atria, and the ventricular septum separating the left and right ventricles. Improper formation of these walls lead to holes, and results in atrial septal defect (ASD) and ventricular septal defect (VSD). Septal defects can be asymptomatic and lead to potentially lethal complications. Given the large amount of images radiologists need to read per day, computer-aided diagnosis is particularly useful to assist in the discovery of defects that are unrelated to the symptoms leading to review.

The present disclosure provides a computational framework for automatic detection of septal defects from 2D contrast-enhanced computed tomography, such as computed tomography angiography (CTA), images to improve efficiency and accuracy of diagnosis. Various embodiments are applicable to a single computed tomography angiography image at a time. To facilitate accurate detection under various imaging settings and disease conditions, an analysis is performed on the blood pools, which are extracted by image thresholding and classified into left pool or combined pools. Shape analysis is performed to extract the shape features, which are input to a classifier for defect detection.

The septum may not be easy to distinguish in a CTA image because of the low contrast between the right blood pool and the septum. Accordingly, embodiments of the present disclosure focus on features of the blood pools. By extracting the blood pools of the left and right atria and ventricles from the image and analyzing the corresponding features, the present disclosure determines whether a patient has an atrial septal defect (ASD), ventricular septal defect (VSD), or no defect. CT imaging is cheaper and more clinically available than MR imaging. CT imaging also requires fewer or no breath-holds and can be performed on patients with an implantable cardioverter defibrillator (ICD). Furthermore, the use of a single 2D image instead of a 3D image sequence lowers the imaging requirement and radiation dose exposure. This also reduces the computation time. The approach and computationally efficient algorithms provided herein address the time requirements for clinical applications and big data studies. It will be appreciated that although several of the examples provided herein are given in terms of the four-chamber view, the present disclosure is applicable to additional views.

Figure 1:
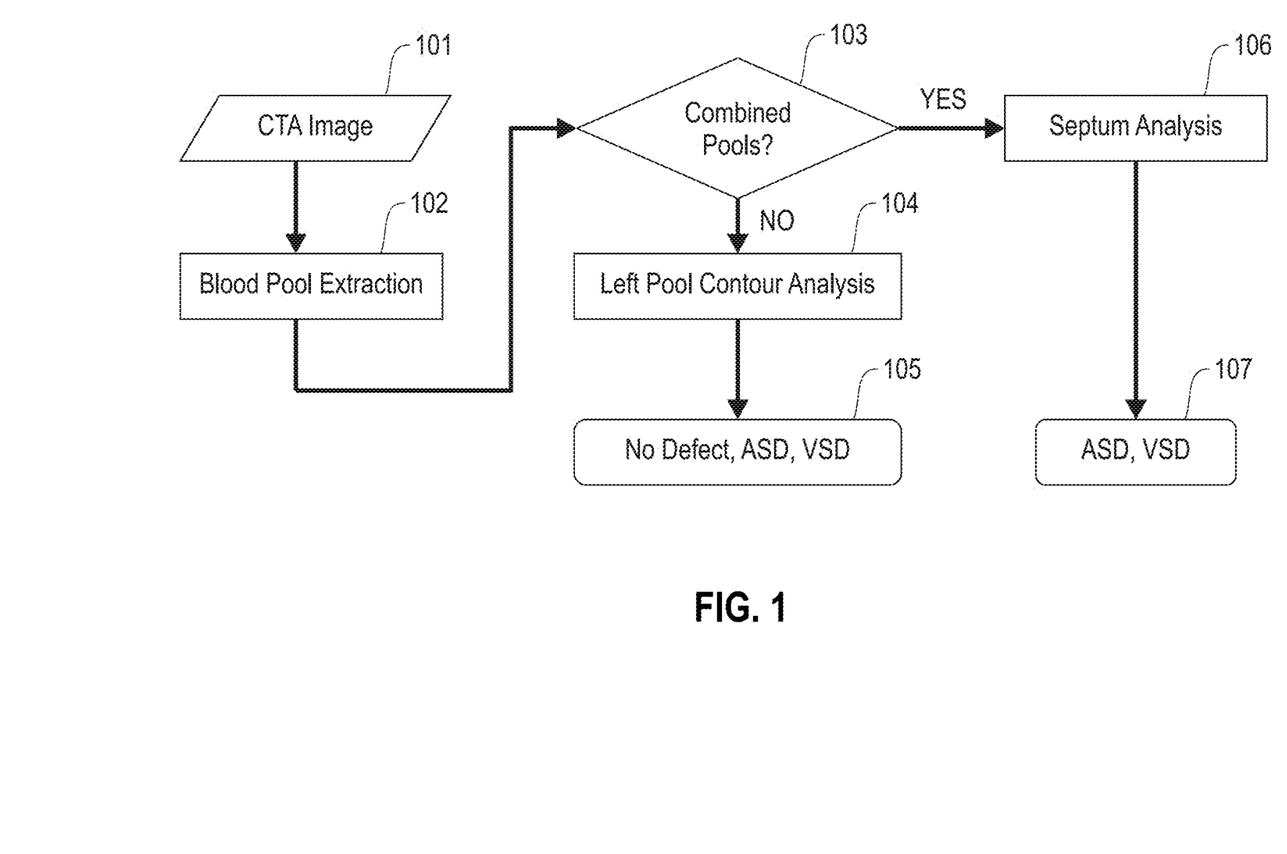
FIG. 1 illustrates a method for septal defect detection according to the present disclosure.

Referring to FIG. 1, a method for septal defect detection according to the present disclosure is illustrated. A CTA image 101, is subject to blood pool extraction 102. The extracted blood pool is analyzed to determine whether it displays combines pools 103. If not, then a left pool contour analysis is conducts 104, yielding an indication 105 of no defect, of atrial septal defect (ASD), or of ventricular septal defect (VSD). If there is a combined pool a septal analysis 106 is conducted, yielding an indication 107 of atrial septal defect (ASD) or of ventricular septal defect (VSD).

In some embodiments, 3D CTA images are received and handled using a slice recognition approach. For example, a convolutional neural network may be used for classifying a 2D slice into one of nine predefined anatomical classes, one of which is the axial four-chamber view. A heart extraction step may be applied to isolate the area depicting the heart from the whole CTA scan, which often covers the upper body. This saves the unnecessary classification of slices where the heart is invisible.

In various embodiments, heart extraction is achieved by image thresholding and morphological operations. As blood pools are usually bright in CTA images, the multilevel Otsu method is used to partition the image into five labels, and the one with the highest mean intensity is chosen. As the chosen label associates with the blood pools, blood vessels, and bones, morphological opening is applied to remove small and thin structures. The bounding box of the largest structure, which is usually the blood pool, is used as the cropping region of the heart. To ensure the entire heart is in the output, the lungs are also extracted using the binary Otsu method. The morphological information of the lungs is used to modify the cropping region when erroneous situations, such as an abnormally small heart, are detected. The cropping region determines the slices to be input to the slice recognition algorithm.

In various embodiments, slice recognition is used to identify the four-chamber slices. Each slice from the heart extraction is input to a slice recognition network to provide the class likelihood for the four chamber view. In some embodiments, slices with likelihood ≥0.8 are included in the analysis. In an exemplary embodiment, transfer learning with AlexNet is used by replacing the output softmax layer with the nine nodes of the anatomical labels.

Figure 2A:
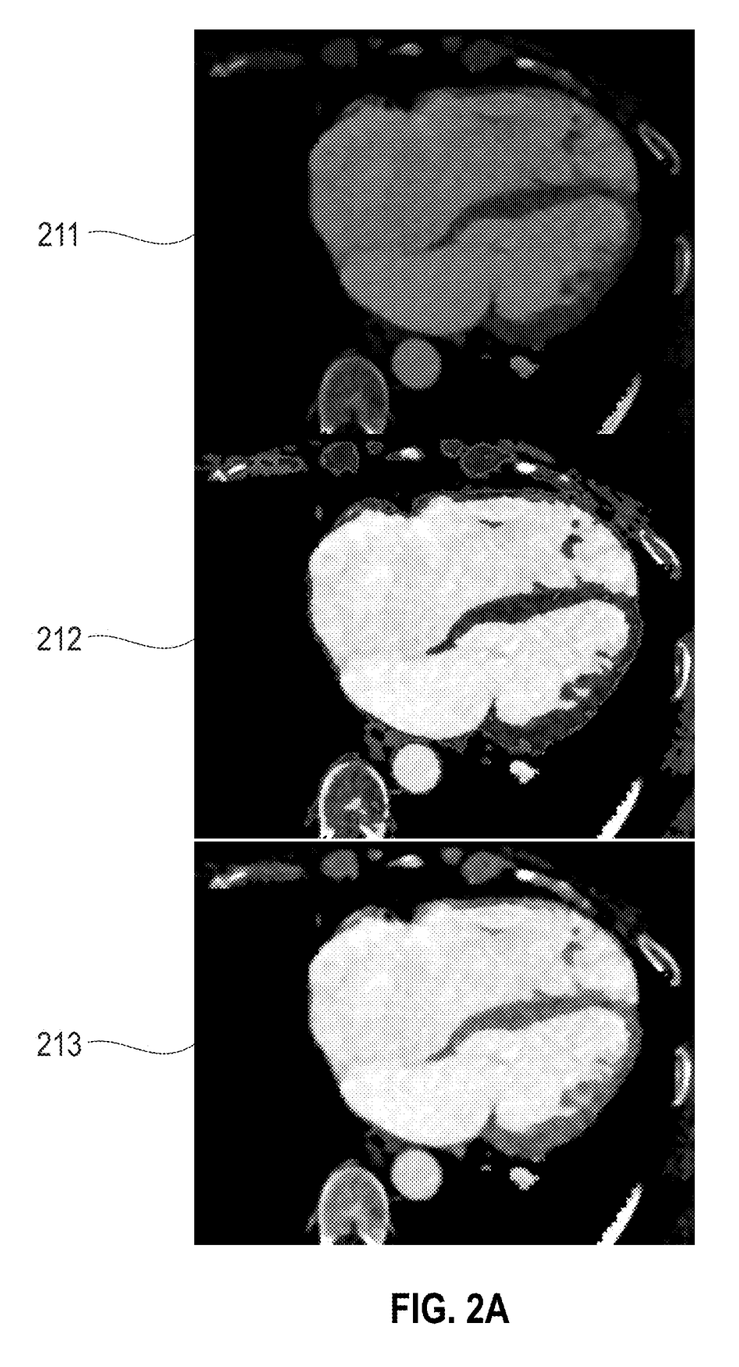
FIGS. 2A-C illustrates blood pool extraction according to embodiments of the present disclosure.
Figure 2B:
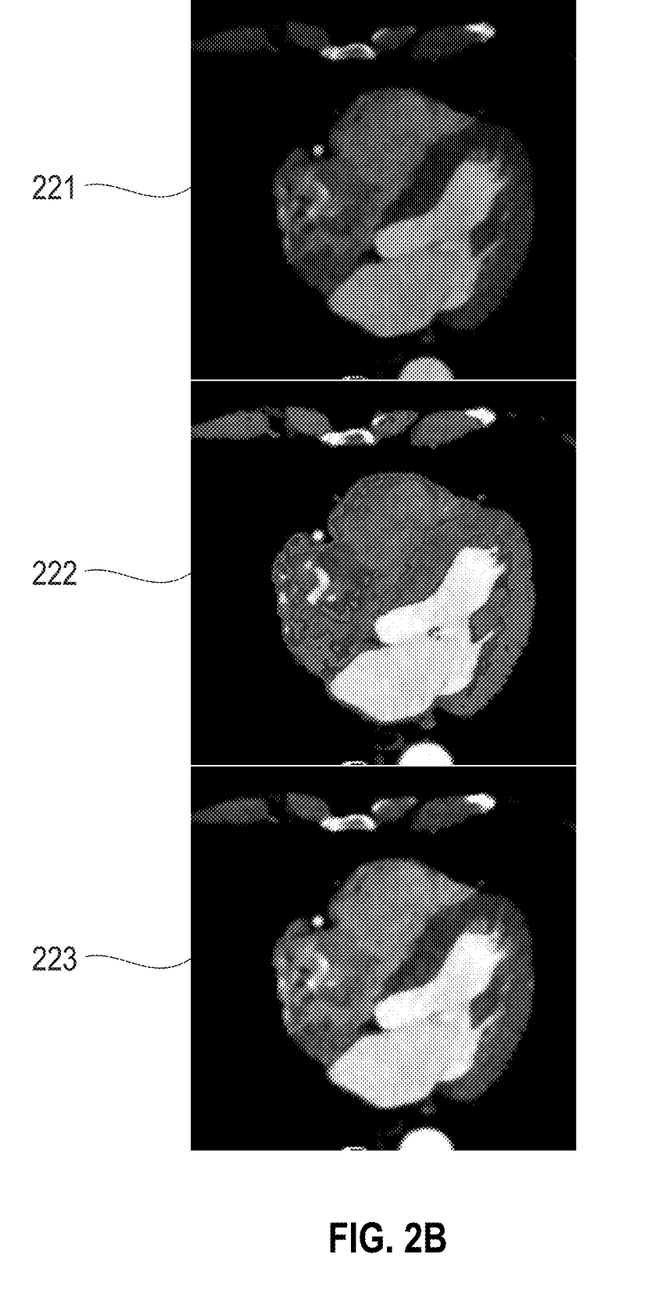
Figure 2C:
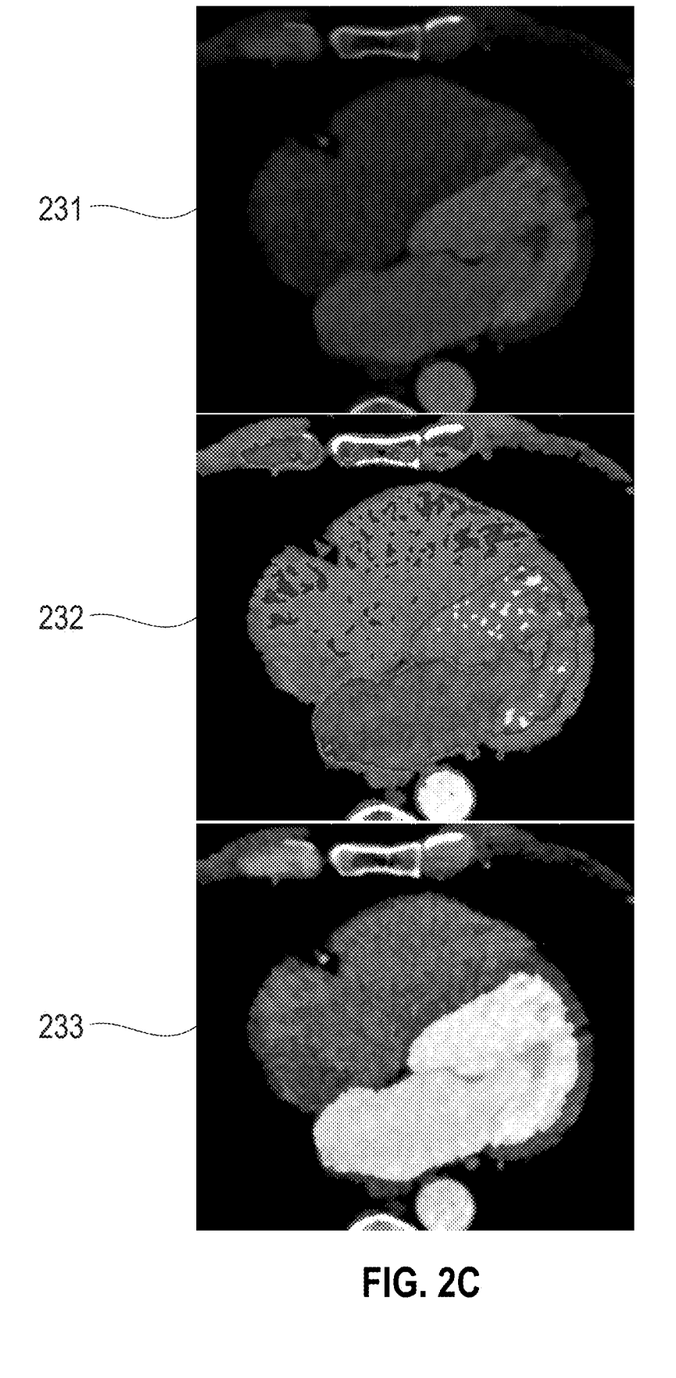

Referring to FIGS. 2A-C, blood pool extraction is illustrated according to embodiments of the present disclosure. CTA images 211, 221, 231 are shown prior to extraction. Images 212, 222, 232 show image thresholding for blood pool candidates, with lighter colors representing labels of increasing mean image intensities. Images 213, 223, 233 show extracted blood pools. In FIG. 2A, a combined pool is shown, indicating ASD. FIGS. 2B-C show no defect.

From four chamber CTA images, two blood-pool patterns can be extracted—the combined left and right blood pools (combined pools) and the left blood pool only (left pool). Combined pools can be observed when there is a hole on the septum and the left and right blood pools have similar image intensities. A left pool can be observed when the right blood pool has lower image intensity than the left one, regardless of the existence of septal defects.

Blood usually has high image intensity in CTA images because of the contrast agent. Therefore, thresholding algorithms such as k-means or Otsu methods can be applied, and the structures of the labels with higher mean intensities can be used as the candidates of the blood pools. The multilevel Otsu method is used in various embodiments as it provides better accuracy than k-means in experiments described herein. Accordingly, such embodiments are independent of absolute image intensity.

The number of labels is important for accurate blood pools extractions. In various embodiments, four labels are used to cover different possibilities. For the combined pools, the label with the largest mean intensity usually provides the appropriate candidates for the blood pools, as illustrated in FIG. 2A. For the left pool, if the right blood pool is distinctively brighter than the myocardium, the appropriate candidates can be provided by the label with the largest mean image intensity, as illustrated in FIG. 2B. Otherwise, the right pool and the myocardium may be classified as the same label, and the label with the largest mean image intensity may correspond to other structures such as bones or aorta, as illustrated in FIG. 2C. As those structures are usually much smaller than the blood pools, such situations can be detected by size thresholding, and the label with the second largest mean image intensity can provide the correct candidates.

As the blood pools are usually larger among the candidates, the object with the most connected pixels is chosen. Shape analysis is then performed to decide between the combined pools and left pool. The elongation of the object is analyzed, which is defined as the ratio between its largest and smallest principal moments of second order. As the left pool is usually more elongated, the object is classified as the left pool if the elongation is larger than the empirical value, 1.8. Otherwise, the location and extent are analyzed. If the object occupies the center region of the image, it is classified as combined pools, otherwise, as left pool.

Figure 3A:
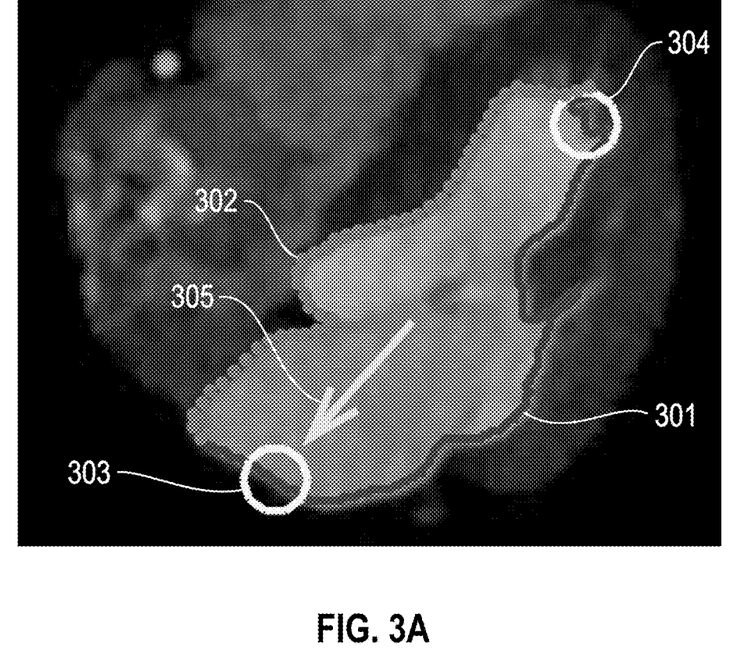
FIG. 3A-B illustrates left-pool feature extraction according to embodiments of the present disclosure.
Figure 3B:
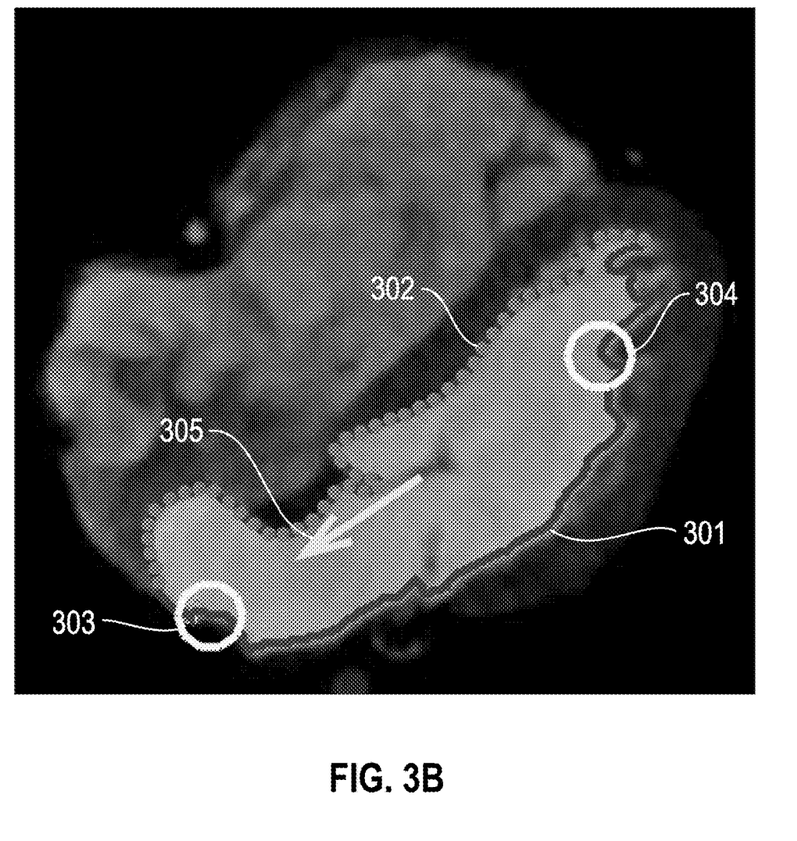

Referring to FIGS. 3A-B, left-pool feature extraction is illustrated according to embodiments of the present disclosure. Solid line 301 illustrates the contour. Dotted line 302 illustrates septal sampling points. Circles 303, 304 illustrated the end points. Arrow 305 illustrates the long axis pointing from the apex to base, starting from the centroid. Features of septal sampling points are used for classification. No defect appears in FIG. 3A, while ASD appears in FIG. 3B.

The left pool associates with no defect, ASD, and VSD. Features can be extracted from the septal part of its contour to provide the diagnostic information. To extract the septal part, the long axis of the blood pool is approximated by its centroid and the principal axis corresponding to the largest principal second order moment, as illustrated in FIG. 3. Two end points on the contour are then computed as the farthest intersection points between the long axis and the contour, and the point near the apex is used as a reference. A vector is constructed from the reference point to each sampling point on the contour, and its scalar projection on the long-axis is computed. Using the scalar projections and the counter-clockwise order of the sampling points, the septal part of the contour can be extracted as the sequence of the sampling points from the minimum to the maximum scalar projection.

To facilitate classification, each septal contour is resampled to a fixed number of equal distance sampling points. In some embodiments, 50 points are used, based on a high detection accuracy in experiments. In various embodiments, additional features may be used that provide good detection accuracy, including: the scalar projections of the sampling points from the apical reference point projected on the long-axis, divided by the maximum scalar projection; the perpendicular distances from the sampling points to the long axis, divided by the maximum among them; and the derivatives of the perpendicular distances along the long-axis vector direction. These features are independent of the actual physical sizes, and are used to classify the no-defect, ASD, and VSD cases.

Figure 4A:
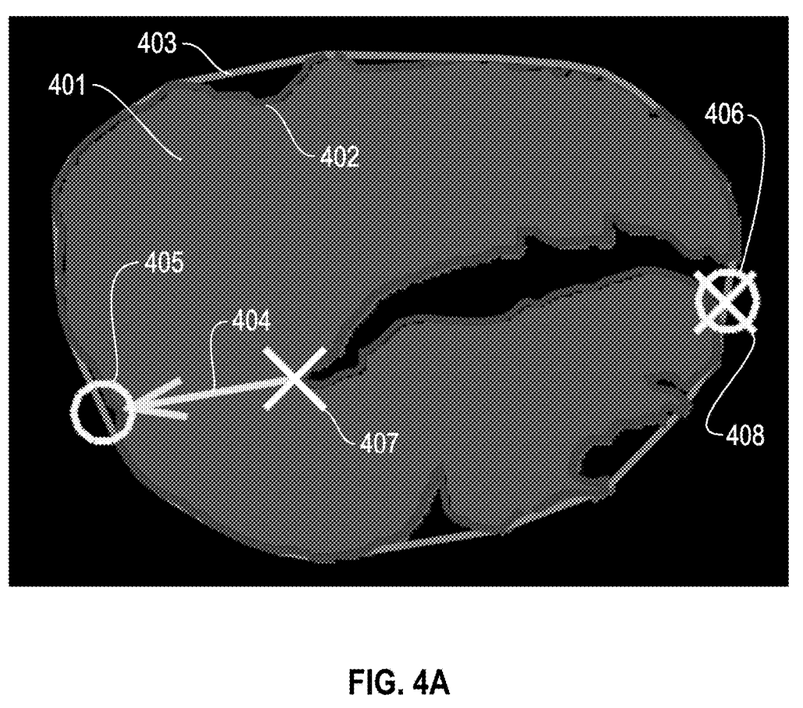
FIGS. 4A-B illustrates combined-pool feature extraction according to embodiments of the present disclosure.
Figure 4B:
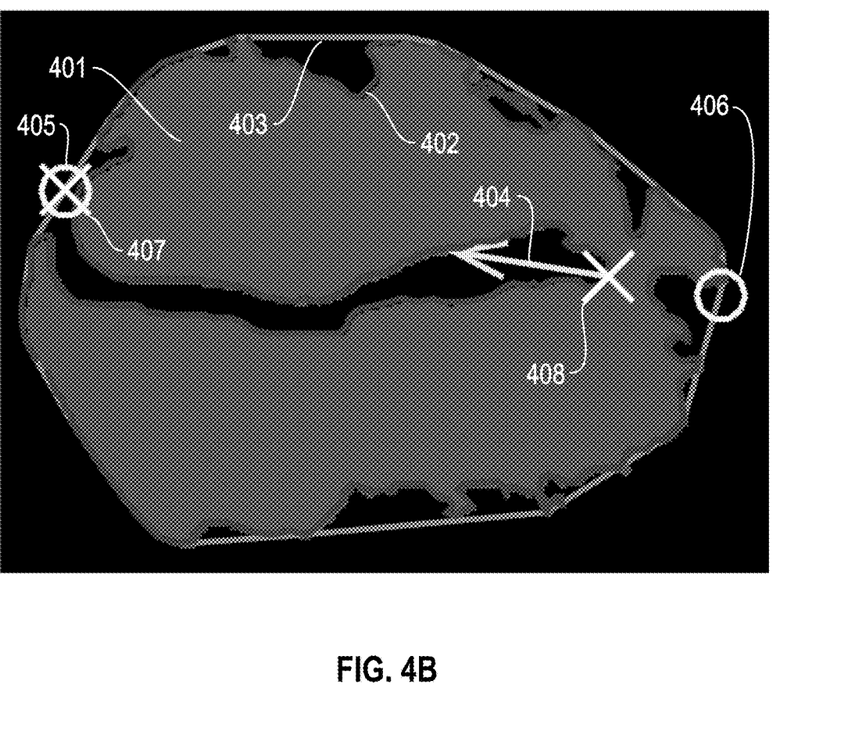

Referring to FIGS. 4A-B, combined-pool features extraction is illustrated according to embodiments of the present disclosure. Combined pool 401 is outlined by contour 402. Convex hull 403 is also depicted. Arrow 404 indicates the long axis pointing from the apex to base, starting from the first septal point. Circles 405, 406 indicate end points on the convex hull. Xs 407, 408 indicate septal points. As noted, features of septal points may be used for classification. FIG. 4A shows ASD, while FIG. 4B shows VSD.

As the septum is usually obvious in the combined pools, its features are used for classification. Two feature points of the septum are computed using convexity defects, as illustrated in FIG. 4. Given a contour and its convex hull, the convexity defects are the concave parts of the contour, and the depth of a defect is defined as the distance between its farthest contour point and the hull. With the shape of the combined pools, the contour point associates with the largest depth among all convexity defects is used as the first septal point. The second septal point is approximated as the midpoint between the two hull vertices of the corresponding convexity defect. To compute the features, two end points on the convex hull are computed as the intersections between the convex hull and the line formed by the two septal points. The scalar projections of the two septal points from the apical end point on the long axis are computed and divided by the distance between the end points. These two projections and their difference are used as the septal features for classifying between ASD and VSD.

As the combined pools and left pool have different features, different models are trained for the classification. For the combined pools, only binary classification between ASD and VSD is required. On the other hand, the left pool associates with no defect, ASD, and VSD, thus multiclass classification is needed. To better handle outliers and to facilitate multiclass classification, the random forest is used in various embodiments.

Experiments were performed on clinical data to validate the above approach. To supplement a collection of 3D DICOM images with reported septal defects, 2D four chamber images from other sources were also used. This is feasible as the present disclosure does not depend on the physical size and absolute image intensity, and only the shape features are used for defect detection. There were 16 no-defect, 21 ASD, and 10 VSD cases, among them 23 cases were 3D images. To facilitate cross-validations with the 2D images, for each 3D image, only the middle slice among the chosen four chamber slices was used. Although the number of samples is limited, the experiments provide the proof of concept for the feasibility and potential of the framework.

The experimental implementation was in Java with SimpleITK and OpenCV. 500 trees were used for the random forest as this provided accurate and consistent results.

The first step of the pipeline for 3D cases is finding the axial four chamber view. The heart extraction and slice recognition steps were performed on all 23 3D cases, which were visually inspected to verify that each selected slice was in fact a four-chamber view image, which were true in all cases.

For blood pools extraction and classification, there were 30 and 17 images classified as left pool and combined pools, respectively. The combined pools did not include any no-defect cases.

For defect detection using the extracted features of the blood pools, leave-one-subject-out cross-validations were performed. Three different experiments were performed, including the classification between no defect and ASD, between no defect and VSD, and among no defect, ASD, and VSD (multiclass). Table 1 shows the detection accuracy of leave-one-subject-out cross validations, the parenthetical given the number of correctly identified cases/number of cases.

TABLE 1

|  | No defect, ASD | No defect, VSD | Multiclass |
| --- | --- | --- | --- |
| Left | 87.5% (21/24) | 86.4% (19/22) | 76.7% (23/30) |
| Combined | 100.0% (13/13) | 100.0% (4/4) | 94.1% (16/17) |
| Overall | 91.9% (34/37) | 88.5% (23/26) | 83.0% (39/47) |

For the two-class experiments, the combined-pool cases had 100% detection accuracies as they did not have no-defect cases. Therefore, the combined-pool features were irrelevant in these experiments. For the multiclass experiments, the ratio between ASD and VSD combined-pool cases was 13:4. Regardless of such imbalance, only one case of VSD was misclassified. This shows that the combined-pool features are useful to distinguish between ASD and VSD.

The detection characteristics of the left-pool features can be depicted from the results of both two-class and multiclass experiments. The performance of the binary classification was better on ASD than on VSD. For the multiclass classification, the performance was lower as expected. The overall performance was promising especially for the classification between no defect and ASD (91.9% accuracy).

The framework was tested on a laptop computer with an Intel i7-4800MQ processor of 2.7 GHz. As some images were 2D, the computation time of slice recognition was not considered. For the features extractions on all 47 images, the total time used was less than 15 seconds. For the 47 leave-one-subject-out cross-validations of the multiclass classification with the pre-computed features, the total time was less than 9 seconds with both training and testing. It will be appreciated that additional speed advantages may be obtained through the use of parallel computing or more efficient programming languages.

The experiments were performed on a single four chamber slice for each 3D image to facilitate cross-validations with the 2D images. In fact, the detection can be applied to all chosen four chamber slices, and algorithms such as voting can be applied for the final decision.

Figure 5:
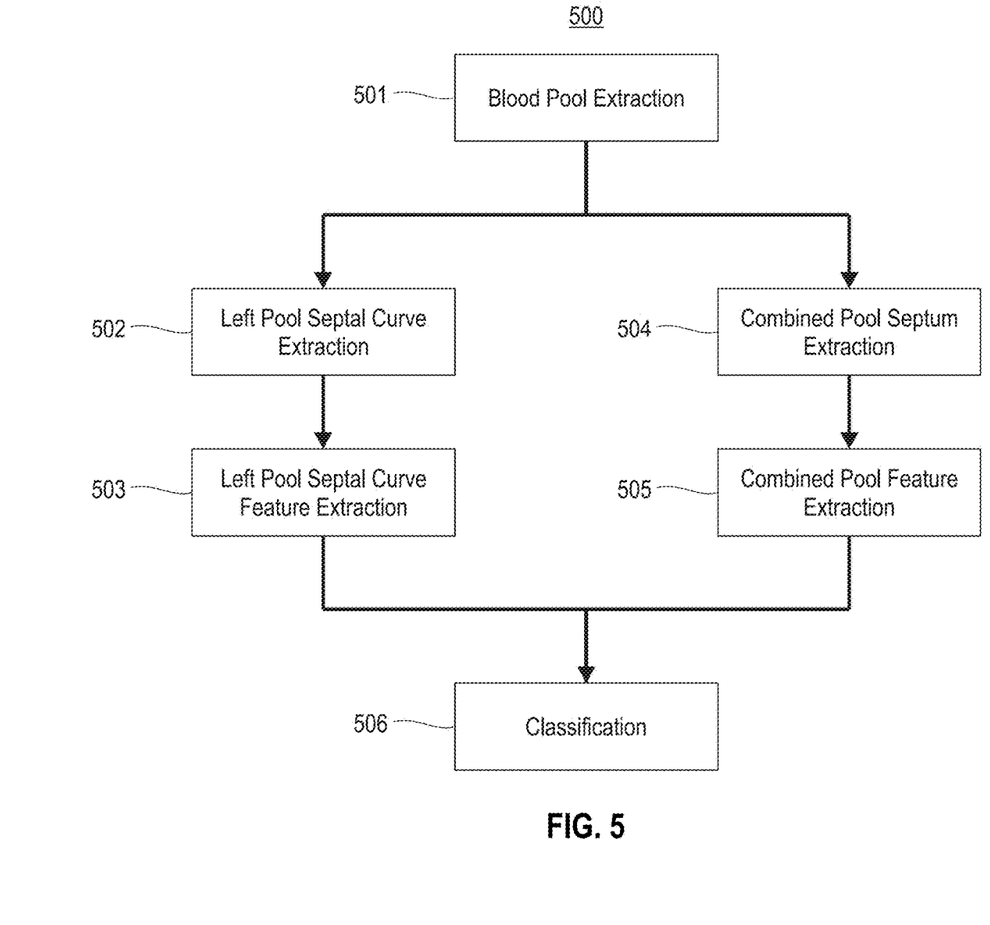
FIG. 5 illustrates a method of septal defect detection according to embodiments of the present disclosure.

Referring to FIG. 5, a method of septal defect detection is illustrated according to embodiments of the present disclosure. At 501, blood pools are extracted and classified. At 502, septal curve extraction is performed for the left pool. At 503, septal curve features extraction is performed for the left pool. At 504, septum extraction is performed for the combined pool. At 505, feature extraction is performed for the combined pool. At 506, classification is performed.

In various embodiments, the blood pools are first extracted in step 501 from the image so that their features can be used for septal defects detection. Blood usually has higher image intensity in CTA images because of the contrast agent. Using the below procedure, the blood pools can be extracted and classified for further analysis.

First, blood-pool candidates are extracted. In CTA images, pixels at blood pools have higher image intensity values than the myocardium. By applying thresholding algorithms, such as k-means or Otsu methods, on the image intensity, blood-pool candidates are extracted as the pixels of the classes with higher mean intensities.

In some embodiments, the image intensities are clustered into three classes, and the image pixels of the class with the highest mean intensity are the candidates.

In some embodiments, the image intensities are clustered into four classes, and the image pixels of the class with the highest mean image intensity are the candidates. If the number of candidate pixels is smaller than a threshold, which indicates the candidates may belong to other structures such as bones, the pixels of the class with the second highest mean intensity are chosen instead.

Second, unnecessary details are removed. The candidates may include structures which are not blood pools. As the blood pools are usually the largest structures in an image, the shape with the largest number of connected pixels is chosen to represent the blood pools.

Third, type classification is performed. The extracted shape can be classified into two types: Left blood pool (left pool), including the left atrium and/or ventricle; Combined left and right blood pools (combined pools), including the left and right pools, with the right pool including the right atrium and/or ventricle. This type implies the existence of holes on the septum/septa.

The elongation of the shape is used to classify if it is a left pool or combined pools. If the elongation is larger than a threshold, it is classified as a left pool. Otherwise, there are two possible conditions: the position of the heart with respect to the image is unknown and the shape is classified as combined pools; the heart is known to be around the center of the image, in which case if the shape is around the center of the image, it is classified as combined pools, otherwise, a left pool. With the extracted left pool or combined pools, further analysis can be performed.

In various embodiments, for the left pool, the part related to the septum is extracted at step 503 for further analysis. Given the shape of the left pool, its contour is extracted and represented by sampling points arranged clockwise or counter-clockwise. The major principal axis of the shape is computed, which usually represents the long axis of the left pool. Using the major principal axis and the order of the sampling points, various methods may be used to obtain the septal part of the contour (septal curve).

In a first method, a line is formed using the major principal axis and a reference point inside the left pool, such as its centroid. The two end points that have the longest distance among the intersection points between the line and the contour are computed. As a result, one end point should be near the base of the heart and another should be near the apex. Using the distances between the sampling points and either end point, with also the given order of the sampling points, the subset of the sampling points representing the septal curve can be extracted.

In a second method, vectors from a reference point to the sampling points are defined. Their scalar projections are then computed on a vector parallel to the major principal axis. Examples of the reference point include the centroid of the left pool, and the end points as in the prior method. Using these scalar projections and the order of the sampling points, the subset of the sampling points representing the septal curve can be extracted.

In various embodiments, septal curve features extraction is performed for the left pool at step 503. The septal curve can be resampled to a fixed number of points for each patient, so that classification techniques such as machine learning methods can be applied on the extracted features. In various embodiments, the features include any combinations of: The scalar projections of vectors from a reference point to the septal sampling points on a vector parallel to the major principal axis, divided by the magnitude of the largest scalar projection; The signed perpendicular distances between the sampling points and a line parallel to the major principal axis, divided by the magnitude of the largest signed perpendicular distance; the angles between the sampling points; the spatial derivatives of prior features; the absolute values of prior features; or the spatial derivative of the absolute values of prior features.

In various embodiments, the septum is extracted from the combined pools at step 504. Using morphological closing, the holes and gaps of the combined pools can be removed to provide a closed shape. Using image arithmetic such as subtraction or logical AND operation, the difference image between the combined pools and the closed shape can be obtained. The septum is then obtained as the shape with the largest number of connected pixels from the difference image.

In various embodiments, feature extraction is performed on the combined pools at step 505. To extract the features of the septum, the major principal axis of the combined pools or the closed shape is computed. A line is formed using the major principal axis and a reference point inside the left pool, such as its centroid. The two end points that have the longest distance among the intersection points between the line and the combined pools or the closed shape are computed. Vectors are defined from a reference point to the pixels of the septum, then their scalar projections are computed on a vector parallel to the major principal axis. The smallest and largest values of the scalar projections divided by the distance of the end points are used as the features.

In various embodiments, the septal status is classified at step 506. In general, machine learning methods such as support vector machine (SVM) and random forests can be applied on the extracted features for classification. Different approaches are used for the left-pool features and the combined-pool features.

The left-pool features can be used to classify three classes: ASD, VSD, and no defects. For such multiclass classifications, one-vs-one or one-vs-all strategy can be applied with binary classifications. Machine learning methods that can intrinsically handle multiclass classification, such as the random forests method, can also be applied. The features can also be used for binary classifications between 1) ASD and VSD; 2) ASD and no defects; 3) VSD and no defects.

The combined-pool features can be used to classify between ASD and VSD. Any classifier supporting binary classifications can be used.

The present disclosure provide computer-aided septal defect detection framework that works on CTA images in four-chamber view. By extracting the blood pools through image thresholding and shape analysis, their shape features are input to a classifier for septal defect detection. Experimental results show high detection performance especially for the classification between no defect and ASD (91.9% accuracy). Together with the short computation time, this framework is particularly suitable for clinical applications.

Figure 6:
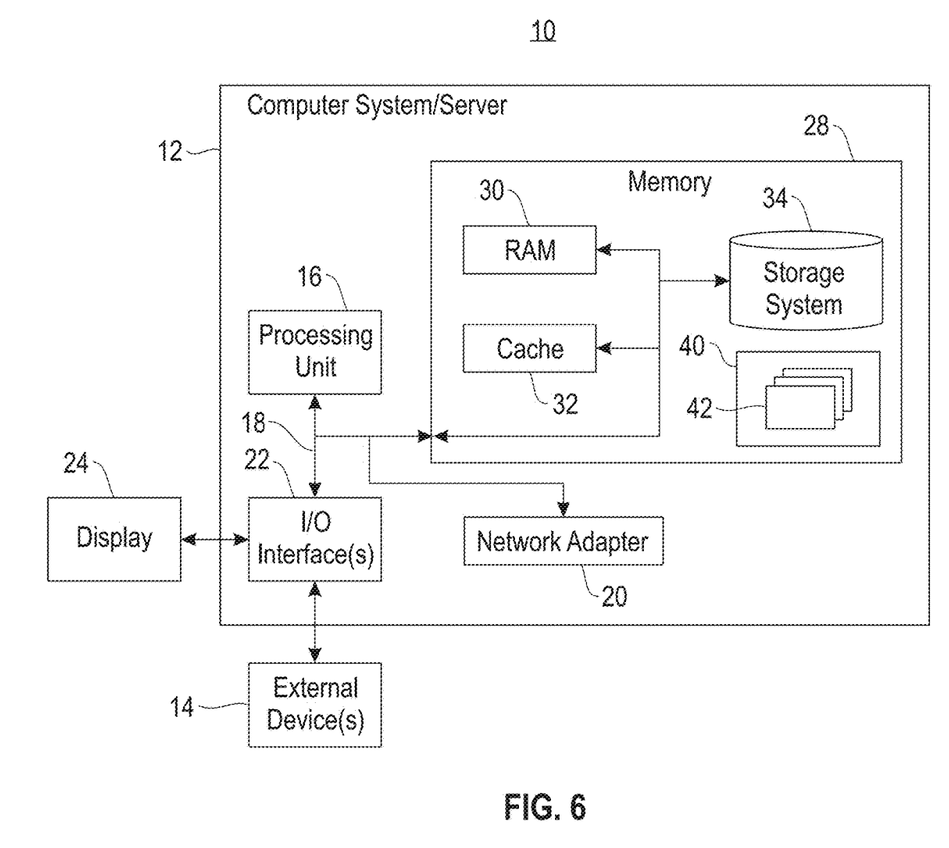
FIG. 6 depicts a computing node according to an embodiment of the present invention.

Referring now to FIG. 6, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 6, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   extracting a blood pool from a CTA image of a heart;
   determining that the blood pool is a left pool;
   extracting a septal curve of the left pool;
   determining a plurality of features of the septal curve;
   classifying the heart as having an atrial septal defect, ventricular septal defect, or no defect based on the plurality of features, wherein classifying the heart comprises applying a support vector machine or random forest.

2. The method of claim 1, wherein extracting the blood pool comprises thresholding.

3. The method of claim 2, wherein the thresholding comprises applying k-means or Otsu methods.

4. The method of claim 2, wherein thresholding comprises clustering image intensities into a predetermined number of classes.

5. The method of claim 1, wherein determining that the blood pool is a left pool comprises determining the elongation of the pool.

6. The method of claim 1, further comprising:
   extracting a 2D CTA image from a 3D CTA study.

7. A method comprising:
   extracting a blood pool from a CTA image of a heart;
   determining that the blood pool is a combined pool;
   determining a plurality of features of the combined pool;
   classifying the heart as having an atrial septal defect or ventricular septal defect based on the plurality of features, wherein classifying the heart comprises applying a support vector machine or random forest.

8. The method of claim 7, wherein extracting the blood pool comprises thresholding.

9. The method of claim 8, wherein the thresholding comprises applying k-means or Otsu methods.

10. The method of claim 8, wherein thresholding comprises clustering image intensities into a predetermined number of classes.

11. The method of claim 7, wherein determining that the blood pool is a combined pool comprises determining the elongation of the pool.

12. The method of claim 7, further comprising:
    extracting a 2D CTA image from a 3D CTA study.

13. A system comprising:
    a computing node comprising a computer readable storage medium having program instructions embodied therewith, the program instructions executable by a processor of the computing node to cause the processor to perform a method comprising:
       extracting a blood pool from a CTA image of a heart;
       determining that the blood pool is a left pool;
       extracting a septal curve of the left pool;
       determining a plurality of features of the septal curve;
       classifying the heart as having an atrial septal defect, ventricular septal defect, or no defect based on the plurality of features, wherein classifying the heart comprises applying a support vector machine or random forest.

14. The system of claim 13, wherein extracting the blood pool comprises thresholding.

15. The system of claim 13, wherein determining that the blood pool is a left pool comprises determining the elongation of the pool.

16. The system of claim 13, the method further comprising:
    extracting a 2D CTA image from a 3D CTA study.

17. A computer program product for septal defect detection, the computer program product comprising a computer readable storage medium having program instructions embodied therewith, the program instructions executable by a processor to cause the processor to perform a method comprising:
    extracting a blood pool from a CTA image of a heart;

determining that the blood pool is a left pool;
extracting a septal curve of the left pool;
determining a plurality of features of the septal curve;
classifying the heart as having an atrial septal defect, ventricular septal defect, or no defect based on the plurality of features, wherein classifying the heart comprises applying a support vector machine or random forest.

18. The computer program product of claim 17, wherein extracting the blood pool comprises thresholding.

19. The computer program product of claim 17, wherein determining that the blood pool is a left pool comprises determining the elongation of the pool.

20. The computer program product of claim 17, the method further comprising:
extracting a 2D CTA image from a 3D CTA study.

* * * * *